United States Patent [19]

Van Dyke, Jr.

[11] 4,339,582
[45] Jul. 13, 1982

[54] QUINOLIZIDINE-PROPIONANILIDE COMPOUNDS

[75] Inventor: John W. Van Dyke, Jr., Elkhart, Ind.

[73] Assignee: Miles Laboratories, Inc., Elkhart, Ind.

[21] Appl. No.: 293,965

[22] Filed: Aug. 18, 1981

[51] Int. Cl.³ .......................................... C07D 455/02
[52] U.S. Cl. .................................... 546/112; 424/263
[58] Field of Search ........................................ 546/112

[56] References Cited

FOREIGN PATENT DOCUMENTS 7810654 10/1978 Switzerland .

OTHER PUBLICATIONS

Rogers et al., *J. Med. Chem.* 18, 1126–1130 (1975).
Quick et al., *Tet. Lett.* 1977 (7), 603–606.

*Primary Examiner*—Alan L. Rotman
*Attorney, Agent, or Firm*—Jerome L. Jeffers

[57] ABSTRACT

Disclosed are quinolizidine-propionanilides having the structural formula:

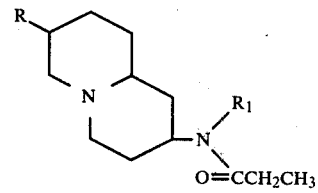

wherein R and $R_1$ are independently phenyl, substituted phenyl or pyridyl.

4 Claims, No Drawings ized in J. Med. Chem. 18, 1126-30 (1975). This

QUINOLIZIDINE-PROPIONANILIDE COMPOUNDS

BACKGROUND OF THE INVENTION

A compound of the formula

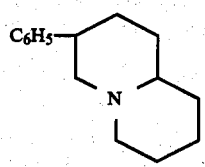

is disclosed in J. Med. Chem. 18, 1126-30 (1975). This compound is reported to have antidepressant activity. In Tet. Lett. 1977 (7), 603-6 there is disclosed a compound of the formula:

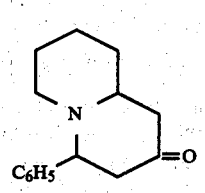

which is used as an intermediate in the synthesis of other compounds. No pharmacological activity is reported for this compound.

Swiss Patent Application 78/10, 654 published Oct. 13, 1978 discloses phenylquinolizidines of the formula:

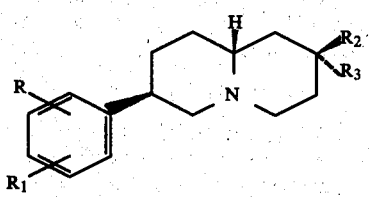

R=H, F, Cl, alkoxy, alkyl, OH or $CH_3$;
$R_1$=H, F, Cl, alkoxy, alkyl;
$R_2$=OH, alkoxy, acyloxy, H;
$R_3$=benzimidazolyl or substituted phenyl.

These compounds are described as having analgesic, antiemetic and tranquilizing activity.

SUMMARY OF THE INVENTION

The present invention involves novel quinolizidine-propionanilides of the formula:

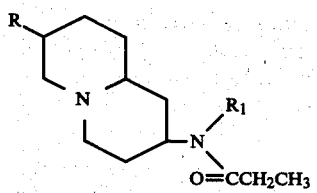

wherein R and $R_1$ are independently phenyl, substituted phenyl or pyridyl. These compounds have strong analgesic activity.

DETAILED DESCRIPTION

The method of preparing the compounds of the present invention is illustrated by Scheme I where R and $R_1$ are as previously described and the substituents on the phenyl group, when it is substituted, can be lower alkoxy of 1 to 4 carbon atoms; halogen, lower alkyl of 1 to 4 carbon atoms or hydroxyl.

SCHEME I

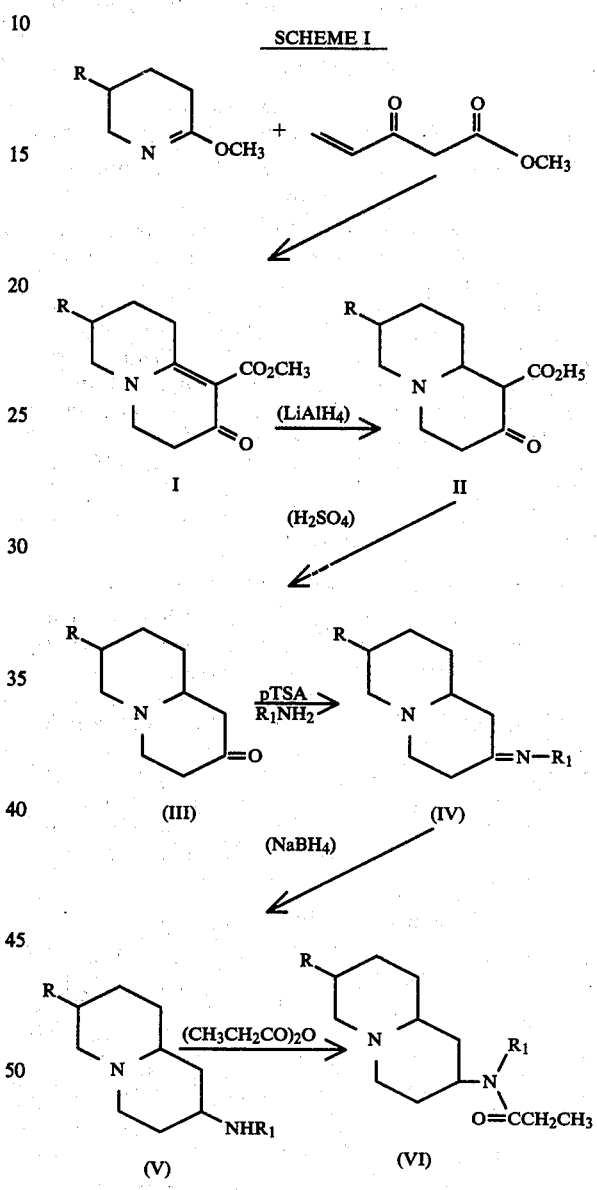

Referring to Scheme I, the preparation is carried out as follows when R and $R_1$ are phenyl: The lactim (2-methoxy-5-phenyl-3,4,5,6-tetrahydropyridine) is reacted with an equivalent amount of 3-oxo-4-pentenoate in a polar solvent such as $CH_3OH$ at room temperature to form Compound I. Compound I is reduced with $LiAlH_4$ (0.75 equiv.) in ether at room temperature. The mixture is stirred for a short time (~1 hour) to provide Compound II which is decarbethoxylated in refluxing dilute $H_2SO_4$ (1.8 M) to produce the ketone (III). The ketone and aniline (or other primary aromatic amine when $R_1$ is other than phenyl) are dissolved in toluene and heated at reflux using a catalytic amount of p-toluenesulfonic acid. A Dean-Starke trap is used to remove the water formed to provide a crude anil IV which is dissolved in alcohol (preferably methanol) and reduced using excess NaBH$_4$ to form anilino Compound V which is dissolved in toluene and excess propionic anhydride whereupon the mixture is refluxed to provide a mixture of isomers which are isolated by chromatographic procedures.

The invention is further illustrated by the following examples:

EXAMPLE 1

Preparation of cis and trans
N-phenyl-N-(7-Phenylquinolizidin-2-yl) Propionamide

1-Carbomethoxy-7-phenyl-3,4,6,7,8,9-hexahydro-2-quinolizone (I)

A solution of methyl 3-oxo-4-pentenoate (14.55 g.) in 100 ml. MeOH was stirred at room temperature while 21.8 g. of the lactim(2-methoxy-5-phenyl-3,4,5,6-tetrahydropyridine)was added portionwise. The solution was stirred at room temperature for 45 hours. A solid had come out of solution and was filtered. Yield, 9.05 g. (m.p. 150°-1°). The filtrate was concentrated to dryness and the semisolid dissolved in toluene, filtered and ether added. After cooling, a pale yellow solid was filtered. Yield, 11.6 g. (m.p. 150°-1°). Total yield, 20.65 g. (63.7% yield) (TR-8006).

Anal. Calcd. for $C_{17}H_{19}NO_3$: C, 71.56; H, 6.71; N, 4.91. Found: C, 7.14; H, 6.71; N, 4.91.

1-Carbomethoxy-7-phenylquinolizidin-2-one (II)

Compound I (15.1 g.) was suspended in ether and LiAlH$_4$ (1.5 g.; 0.75 equiv.) was added portionwise at room temperature. The mixture was stirred for 1 hr. at room temperature. The mixture was treated with wet THF and the mixture filtered. The filtrate was treated with CHCl$_3$/H$_2$O, the CHCl$_3$ separated, dried and the solvent removed in vacuo. Yield, 9 g. The filter-cake was stirred repeatedly with CHCl$_3$ and an additional 4.1 g. of material was obtained. The 13.1 g. was chromatographed on a silica gel column. Compound II was eluted with CHCl$_3$. Yield, 6.82 g. (44.9% yield).

7-Phenylquinolizidin-2-one (III)

The ketoester (II) (6.82 g.) was dissolved in 50 ml. 1.8 M H$_2$SO$_4$ and the mixture refluxed overnight. The solution was cooled and made alkaline with Na$_2$CO$_3$. The organic material was extracted with CHCl$_3$, dried and solvent removed. Yield, 5.6 g. Some ester was still present so the mixture was recycled. The reaction was worked up as above. Yield, 5.25 g. (96.5% yield).

2-Phenylimino-7-phenylquinolizidine (IV)

The ketone (III) (5.25 g.) was dissolved in 100 ml. toluene and 2.13 g. aniline. A small amount of pTSA was added and the solution was refluxed overnight using a Dean-Starke trap. The solvent was removed in vacuo Yield, 6.9 g. The semi-solid still had some ketone present (IR spectrum) so the residue was recycled using 1 g. aniline. The reaction was worked up as above and the crude anil showed no ketone. Yield, 7.2 g. (6.97 g. theoretical; probably excess aniline present).

2-Anilino-7-phenylquinolizidine (V)

The crude anil (IV) (7.2 g.) was dissolved in MeOH (100 ml.), cooled in an ice bath and then NaBH$_4$ (3.6 g.) added portionwise. The mixture was refluxed for 1 hr. and cooled. The solvent was removed and the residue treated with EtOAc/H$_2$O. The EtOAc extracts were combined, dried over MgSO$_4$ and solvent removed in vacuo. Yield, 6.7 g. The TLC showed two spots (most likely two isomers). The mixture was run through a HPLC using EtOAc/acetone (5:1). The mixture was not easily separated and the main portion (4 g.) was still a mixture. The mixture was carried through the rest of the synthesis. Also obtained was the fast component pure (0.7 g.) and the slow component pure (0.4 g.)

N-Phenyl-N-(7-phenylquinolizidin-2-yl) Propionamide (VI)

The anilino mixture (4 g.) was dissolved in toluene (100 ml.) and propionic anhydride (3 g.) added. The solution was refluxed 18 hours. The solution was treated three times with aqueous Na$_2$CO$_3$, the toluene dried over MgSO$_4$ and the solvent removed in vacuo. Yield, 4.7 g. (99.5% crude yield). The product showed four spots on TLC (different isomers).

The mixture was separated into trans (isomer I) and cis (isomer II) isomeric forms as follows:

Isomer I (MLS-8482)

The mixture was chromatographed on a silica gel column. Eluting with CHCl$_3$ gave a fast moving isomer pure (2.1 g.) (one spot on TLC) (44.4% yield). The viscous liquid was crystallized from Skelly B which is essentially normal hexane, boiling range 60°-71° C. Yield, 1.4 g. (29.6% yield) (m.p. 129°-130°).

Anal. Calcd. for $C_{24}H_{30}N_2O$: C, 79.51; H, 8.34; N, 7.73. Found: C, 79.21; H, 8.20; N, 7.49.

Isomer I appeared to have a trans fused ring juncture and the phenyl and propionamide groups most likely are in the equitorial position (based on IR and NMR analyses). An additional 1.46 g. of crude isomer I was obtained in rechromatography (see isomer II).

Isomer II (MLS-8493)

Additional eluting with CHCl$_3$ and then EtOAc gave a mixture of isomers. The mixture was rechromatographed. The material eluted with acetone/MeOH (1:1) (0.6 g.) showed one spot on TLC. The viscous liquid was treated with HCl in MeOH, the solution treated with acetone and concentrated. ETOAc and ether were added and the mixture cooled. The solid was filtered and dried. Yield, 300 mg. (m.p. 230°-2°). The solid was recrystallized from MeOH/acetone/EtOAc and dried. Yield, 220 mg. (m.p. 234°-6°) (4.65% yield).

Anal. Calcd. for $C_{24}H_{30}N_2O·HCl$: C, 72.25; H, 7.83; N, 7.02. Found: C, 72.06; H, 8.00; N, 6.68.

Isomer II appeared to have a cis fused ring juncture (based on IR and NMR analyses).

EXAMPLE II

The compounds prepared in Example I were tested for antinociceptive activity in the manner described hereinafter. Since these compounds have some structural similarity to Fentanyl,

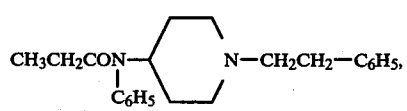

this compound was also tested.

METHODS

(a) Mouse Acetic Acid Writhing Test

Male albino CD-1 mice (18–22 g.) were used for this study. A modification of the Whittle, Brit. J. Pharmacol., 22:246 (1964), procedure was used. The test drug was given by subcutaneous injection 15 min. prior to an intraperitoneal injection of 0.5% acetic acid (0.4 ml.). The number of writhes per group of 5 mice were counted for 20 min., starting 5 min. after the acetic acid injection. Analgesic potency was calculated from the difference between the test groups snd their controls by the following formula.

$$\% \text{ Inhibition} = \frac{100 \times \# \text{ Writhes (control group)} - \# \text{ controls (treated gp)}}{\# \text{ Writhes (control group)}}$$

The data at each dosage level was plotted on log probit paper. The $ED_{50}$ and 95% confidence limits were calculated by the method of Litchfield and Wilcoxon, *J. Pharmacol. Exp. Ther.*, 96, 99–113, (1949). For oral studies, the acetic acid was administered 25 min. after the drug administration.

(b) Rat Tail-Flick Procedure

Male albino Wistar rats (100–150 g.) were used for this study. The method described by Harris and Pierson, *J. Pharmacol. Exp. Ther.*, 143, 141–148 (1964) was used. Two control reaction times were determined 30 min. apart. The test compounds were administered subcutaneously and reaction times were then determined 20 min. later. A 10 second cutoff time was used. The % maximal possible effect (MPE) is calculated by:

$$\% \text{ MPE} = 100 \times \frac{\text{Reaction Time (Treated Group)} - \text{Reaction Time (Control Group)}}{10 - \text{Reaction Time (Control Group)}}$$

The data was plotted graphically using log probit paper and the $ED_{50}$ with 95% confidence limits were calculated by the method of Litchfield and Wilcoxon *J. Pharmacol. Exp. Ther.*, 96, 99–113, (1949).

TABLE 1

| Compound | Antinociceptive Activity of TR-8482, TR-8493, and Fentanyl | |
|---|---|---|
| | Writhing Test $ED_{50}$ (±95% C.L.) mg./kg. | Tail Flick $ED_{50}$ (±95% C.L.) mg./kg. |
| Fentanyl | 0.013 (0.006–0.027) | 0.026 (0.020–0.040) |
| TR-8482 | 0.004 (0.002–0.01) | 0.015 (0.011–0.019) |
| TR-8493 | 0.092 (0.01–1.29) | 0.56 (0.44–0.71) |

Results

The results of the antinociceptive tests are reported in Table 1. TR-8482 was the most potent compound tested and was considerably more active in both procedures than the isomeric TR-8493. All three compounds caused behavioral effects in the rats and mice, which are characteristic of the opiate class of compounds.

What is claimed is:

1. Quinolizidine-propionanilides characterized by the structural formula:

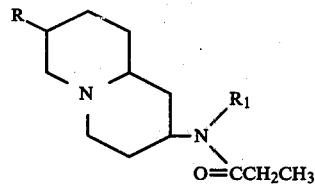

wherein R and $R_1$ are independently phenyl, substituted phenyl wherein the substituents are lower alkoxy of 1 to 4 carbon atoms, halogen, lower alkyl of 1 to 4 carbon atoms or hydroxyl or pyridyl.

2. The compounds of claim 1 wherein R and $R_1$ are phenyl.

3. The compound of claim 2 in its isomeric form having a trans fused ring juncture.

4. The compound of claim 2 in its isomeric form having a cis fused ring juncture.

* * * * *